United States Patent [19]

Sapp

[11] Patent Number: 5,434,664
[45] Date of Patent: Jul. 18, 1995

[54] CAPILLARY FLOWCELL FOR MULTIPLE WAVELENGTH DETECTION

[75] Inventor: Edwin Sapp, Hillsdale, N.J.

[73] Assignee: Perkin-Elmer Corporation, Norwalk, Conn.

[21] Appl. No.: 227,914

[22] Filed: Apr. 15, 1994

Related U.S. Application Data

[63] Continuation of Ser. No. 802,131, Dec. 3, 1991, abandoned.

[51] Int. Cl.$^6$ ............................................. G01N 21/05
[52] U.S. Cl. ................................... 356/244; 356/246; 356/440
[58] Field of Search .................... 356/246, 244, 440

[56] References Cited

U.S. PATENT DOCUMENTS

| | | | |
|---|---|---|---|
| 4,991,958 | 2/1991 | Garner | 356/244 |
| 5,037,199 | 8/1991 | Hlousek | 356/246 |

FOREIGN PATENT DOCUMENTS

| | | | |
|---|---|---|---|
| 0422448 | 4/1991 | European Pat. Off. | 356/440 |

OTHER PUBLICATIONS

Albin et al "Fluorescence Detection in Capillary Electrophoresis: Evaluation of Derivatizing Reagents & Techniques"; Analytical Chemistry, vol. 63 #5 Mar. 1, 1991 pp. 417–422.

Kobayashi et al; "Photodiode array Detection in High--Performance Capillary Electrophoresis", J. Chrom. 480(1989; pp. 179–184).

Moring et al., "Analytical Aspects of an Automated Capillary Electrophoresis System", LC:GC 8(1):34–46 (1990).

Sepaniak et al., "Instrumental Developments in Micellar Electrokinetic Capillary Chromatography", J. Chrom. 480 (1989):185–196.

*Primary Examiner*—Vincent P. McGraw
*Attorney, Agent, or Firm*—Karen S. Perkins; Paul D. Grossman

[57] ABSTRACT

A capillary flowcell of this invention comprises a holding means including an optical axis, the optical axis being defined by, in sequential order, (a) a first (entrance) aperture, (b) a first lens, (c) a capillary tube having its long axis centered across the optical axis, and (d) a second lens. The first lens focuses electromagnetic radiation from the entrance aperture passes through the inner diameter of the capillary tube, thus maximizing the signal generated by the analyte within the capillary tube. The second lens focuses electromagnetic radiation which has passed through the capillary tube. Methods and apparatus pertaining to the flowcell are given.

5 Claims, 3 Drawing Sheets

CAPILLARY FLOWCELL FOR MULTIPLE WAVELENGTH DETECTION

Continuation of Ser. No. 07/802,131 filed Dec. 3, 1991, abandoned.

TECHNICAL FIELD

This invention relates to an improved capillary flowcell apparatus for measuring absorbance of radiation, especially optical radiation, in a multiple wavelength detector (MWD).

BACKGROUND OF THE INVENTION

Optical absorbance across a capillary flowcell is used to determine the presence and/or concentration of an analyte within the capillary.

The basic optical configuration of a multiple wavelength detector is different from that of a variable wavelength detector. However, each type of detector is often configured as a dual beam design, with a flowcell containing analyte(s) in one beam, and a reference flowcell in an alternate reference beam. Such designs permit the determination of lower concentrations of analyte by compensating, for example, for fluctuations in source energy, and reduction of signal variation as a function of wavelength. Electromagnetic radiation which is delivered through the analyte 16 and to the detector 22 (i.e., the signal) competes with electromagnetic radiation which is delivered to the detector 22 without having passed through the analyte 16 (i.e., "noise").

In a variable wavelength detector, broad-band optical radiation from a source is passed through a wavelength selection device such as a monochromator. A narrow, nearly monochromatic band of electromagnetic radiation is selected and focused upon the entrance aperture of the flowcell. Optical radiation which is not scattered or absorbed by the analyte(s) in the flowcell is transmitted through the flowcell, and is converted to an electrical signal by a detector element. If the detector element is sufficiently sensitive and of sufficient area to intercept the transmitted optical beam, it is not necessary to refocus the beam. Variable wavelength detectors of the prior art (which determine a single wavelength of electromagnetic radiation, $s\lambda$), are shown in FIG. 1 and in FIG. 2.

FIG. 1 shows a diagrammatic representation of the path of light through a capillary flowcell in a variable wavelength detector. Monochromatic light at a single wavelength ($s\lambda$) is emitted from an electromagnetic radiation source 10. Electromagnetic radiation (shown as arrows) enters the flowcell 12 by passing through a mask 13 at the entrance aperture 14. The mask 13 is placed to restrict optical radiation which would not pass through the inner diameter of the capillary (and thus the analyte) within the flowcell. The electromagnetic radiation passes through the capillary tube wall 16 and through the analyte 18 contained within the capillary tube. Electromagnetic radiation which has passed through the analyte 18 and which then passes through the exit aperture 20 is converted to an electrical signal by a detector element 22. The optical axis $\alpha$ of the flowcell system is shown for reference purposes.

FIG. 2 shows a diagrammatic representation of the path of light through an alternate capillary flowcell in a variable wavelength detector. Monochromatic light at a single wavelength ($s\lambda$) is emitted from an electromagnetic radiation source 10. Electromagnetic radiation (shown as arrows) enters the flowcell 12 at the entrance aperture 14. A spherical ball lens 15 is then used to reimage the entrance aperture 14 onto the inner diameter of the capillary tube 16 containing the analyte 18. The focused electromagnetic radiation passes through the capillary tube 16 wall and through the analyte 18 contained within the capillary tube. Electromagnetic radiation which has passed through the analyte 18 and which passes through the exit aperture 20 is converted to an electrical signal by a detector element 22. The optical axis $\alpha$ of the flowcell system is shown for reference purposes.

In a multiple wavelength detector, a beam of optical radiation including a multiplicity of wavelengths is focused onto a flowcell. The analyte(s) in the flowcell may absorb optical radiation at a multiplicity of different wavelengths. Optical radiation which is not absorbed by the analyte(s) in the flowcell is transmitted through the flowcell, and through a polychromator. The polychromator disperses the transmitted optical radiation into many narrow bands, as a function of band wavelength. Each narrow band is focused onto a different detector element in a detector array, and is converted to an electrical signal. The absorbance of the analyte(s) in the flowcell is thus measured as a function of wavelength absorption or transmission of many different wavelengths. A multiple wavelength detector such as that found in the prior art, having a beam of multiple wavelength of electromagnetic radiation (m$\lambda$), is shown in FIG. 3. Representative wavelengths ($\lambda_1$, $\lambda_2$, and $\lambda_3$) are shown after separation by the polychromator.

FIG. 3 shows a diagrammatic representation of the path of light through a capillary flowcell in a multiple wavelength detector. Polychromatic light at various wavelengths (m$\lambda$) is emitted from an electromagnetic radiation source 10. Electromagnetic radiation (shown as arrows) enters the flowcell 12 by passing through a mask 13 at the entrance aperture 14. The mask 13 is placed to restrict optical radiation which would not pass through the inner diameter of the capillary (and thus the analyte 18) within the flowcell. The electromagnetic radiation passes through the capillary tube wall 16 and through the analyte 18 contained within the capillary tube. Electromagnetic radiation which has passed through the analyte 18 and which passes through the exit aperture 20 is split into discrete bands (such as $\lambda_1$, $\lambda_2$ and $\lambda_3$) by the polychromator 24. As shown, the polychromator can include an entrance aperture 21. Alternatively, the exit aperture 20 of the flowcell 10 can act as the entrance aperture for the polychromator. Each discrete wavelength of electromagnetic radiation is then converted to an electrical signal by discrete detector elements 22. The optical axis $\alpha$ of the flowcell system is shown for reference purposes.

The fundamental design differences between variable wavelength detectors and multiple wavelength detectors place conflicting demands upon flowcell design, especially with respect to optical radiation transmitted through the analyte. Variable wavelength detectors are often designed such that the beam of optical radiation does not require focusing after passing through the analyte. Rather, the beam is uninterrupted between the capillary containing the analyte and the detector element. Multiple wavelength detectors generally require that the beam be refocused for the polychromator after the beam has passed through the analyte sample. The exit aperture of the flowcell can serve as the entrance aperture for the polychromator.

The presence of a capillary column within the flowcell restricts flowcell design. Because chromatic integrity is maintained by minimizing off-column chromatic dispersion, on-column detection is usual. In on-column detection, the capillary forms part of the flowcell.

Albin et al., "Fluorescence Detection in Capillary Electrophoresis: Evaluation of Derivatizing Reagents and Techniques", Anal. Chem. 63 (1991) describe a capillary electrophoresis fluorescence detector. A single sapphire lens is used to focus the monochromatic beam before the beam is passed through the capillary flowcell.

Kobayashi et al. ("Photodiode Array Detection in High-Performance Capillary Electrophoresis", J. Chrom. 480 (1989):179–184) describe replacement of a standard cell of a spectrometer with a capillary. The light intensity of the apparatus was decreased to prevent saturation of the diode array.

Moring et al., "Analytical Aspects of an Automated Capillary Electrophoresis System", LC:GC 8(1):34–46 (1990) describes a variable wavelength detector in which one sapphire lens is used to focus the monochromatic light prior to the time the beam is focused on the capillary flowcell.

A capillary flowcell is described in Sepaniak et al., "Instrumental Developments in Micellar Electrokinetic Capillary Chromatography", J. Chrom. 480 (1989):185–196. The capillary flowcell is produced by removing a portion of the capillary coating, epoxying the capillary between two microscope slides, attaching the capillary and slides to a bracket, painting the front face of the apparatus black, and using an argon laser to etch the painted section. The flowcell is completed by masking all but a small portion with electrical tape. The flowcell is described for use with each of a variable wavelength detector and a multiple wavelength detector. When the flowcell is used in a multiple wavelength detector, a beam of optical radiation originates in a deuterium lamp, passes first through the capillary, and then through two separate lenses before it is focused at the entrance of the spectrometer.

SUMMARY OF THE INVENTION

A capillary flowcell of this invention comprises a holding means including an optical axis, the optical axis being defined by, in sequential order, (a) a first (entrance) aperture, (b) a first lens, (c) a capillary tube having its long axis centered across the optical axis, and (d) a second lens. The first lens focuses electromagnetic radiation from the entrance aperture to pass through the inner diameter of the capillary tube, thus maximizing the signal generated by the analyte within the capillary tube. The second lens focuses electromagnetic radiation which has passed through the capillary tube. Generally, the second lens focuses the electromagnetic radiation through the exit aperture of the flowcell or through the entrance aperture of a polychromator, thus maximizing the "signal" and minimizing the amount of light which is scattered to produce "noise". More preferably, the entrance aperture of the polychromator is the exit aperture of the flow cell.

The holding means preferably includes a means for holding a capillary tube precisely, so that the center of the capillary tube is held directly across the optical axis of the holding means. The holding means can conveniently comprise two mating parts, the union of the parts providing a channel through which the capillary tube is held.

DISCLOSURE OF THE INVENTION INCLUDING BEST MODE

The subject invention is a flowcell design which provides enhanced imaging capability for flowcell function with a polychromator in a multiple wavelength detector. It provides increased throughput to allow lower limits of detection of analytes in a capillary; a means of locating and holding the capillary in place while allowing easy replacement of the capillary; and the ability to substitute for a typical liquid chromatography flowcell in a standard multiple wavelength detector.

Similar numbers refer to similar function throughout the Figures. The figures are drawn for clarity and are not drawn to scale.

Figure 1:
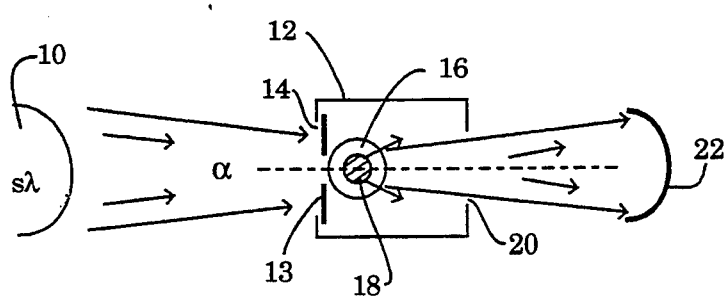
FIG. 1 shows a diagrammatic view of a variable wavelength detector and capillary flowcell of the prior art.
Figure 2:
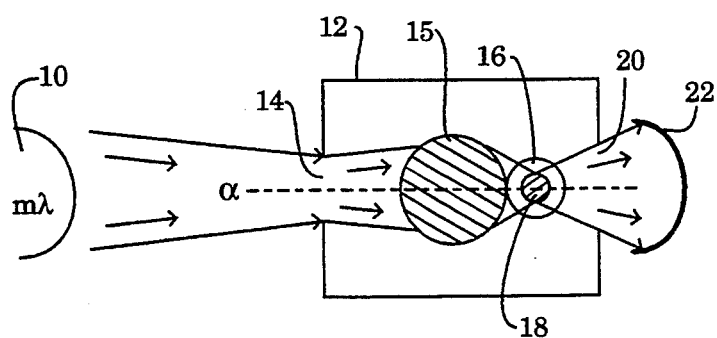
FIG. 2 shows a diagrammatic view of an alternate variable wavelength detector and capillary flowcell of the prior art.
Figure 3:
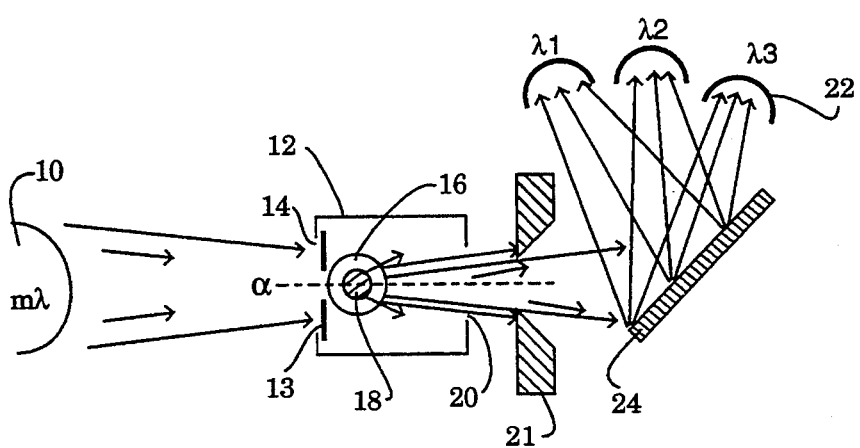
FIG. 3 shows a diagrammatic view of a multiple wavelength detector and capillary flowcell of the prior art.
Figure 4:
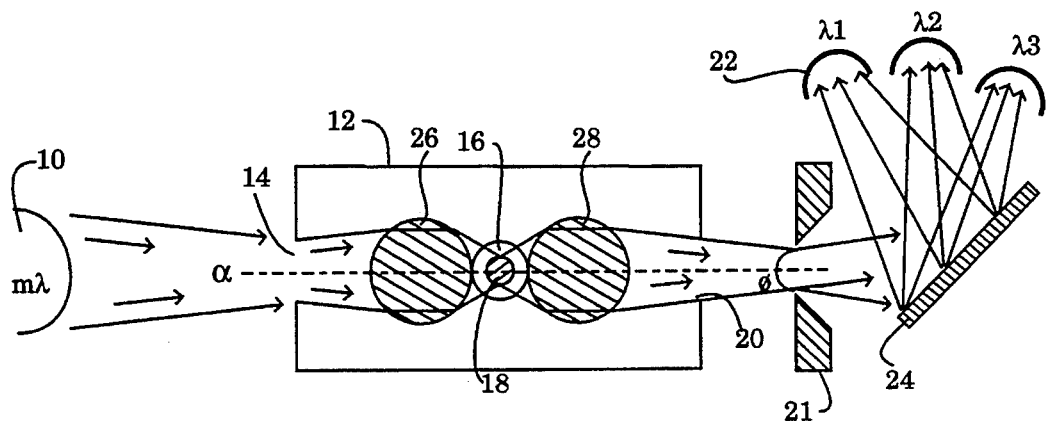
FIG. 4 shows a diagrammatic view of a variable wavelength detector and capillary flowcell of this invention.

FIG. 4 shows a diagrammatic representation of the path of a light beam through a capillary flowcell of this invention. Polychromatic light at various wavelengths (m$\lambda$) is emitted from an electromagnetic radiation source 10. Convergent incident electromagnetic radiation (shown as arrows) enters the flowcell 12 at the entrance aperture 14. The electromagnetic radiation passes through a first lens 26. The first lens 26 focuses the electromagnetic radiation entering the flowcell at the entrance aperture onto the analyte 18 contained within the inner diameter of the capillary tube 16. This focusing causes the electromagnetic radiation to pass substantially through the analyte 18 contained within the inner diameter of the capillary tube 16. Such focusing of the electromagnetic radiation beam maximizes the amount of electromagnetic radiation which passes through the analyte, and thus maximizes the "signal". It also minimizes the amount of electrical radiation which does not pass through the analyte and appears as "noise".

Electromagnetic radiation which has passed through the analyte 18 then passes through the second lens 28. The second lens focuses the "signal" to pass through the exit aperture 20 and/or the entrance aperture 21 of the polychromator 24 while minimizing the "noise" which is transmitted. Preferably, the illuminated area of the analyte is reimaged by the second lens onto the entrance aperture of the polychromator. In a preferred embodiment, the convergent exit angle ($\phi$) of the flowcell matches the entrance angle of the polychromator. The polychromator 24 splits the beam into discrete bands (shown as $\lambda_1$, $\lambda_2$ and $\lambda_3$). As with the previous embodiments, each discrete wavelength of electromagnetic radiation is then converted to an electrical signal by discrete detector elements 22.

Figure 5:
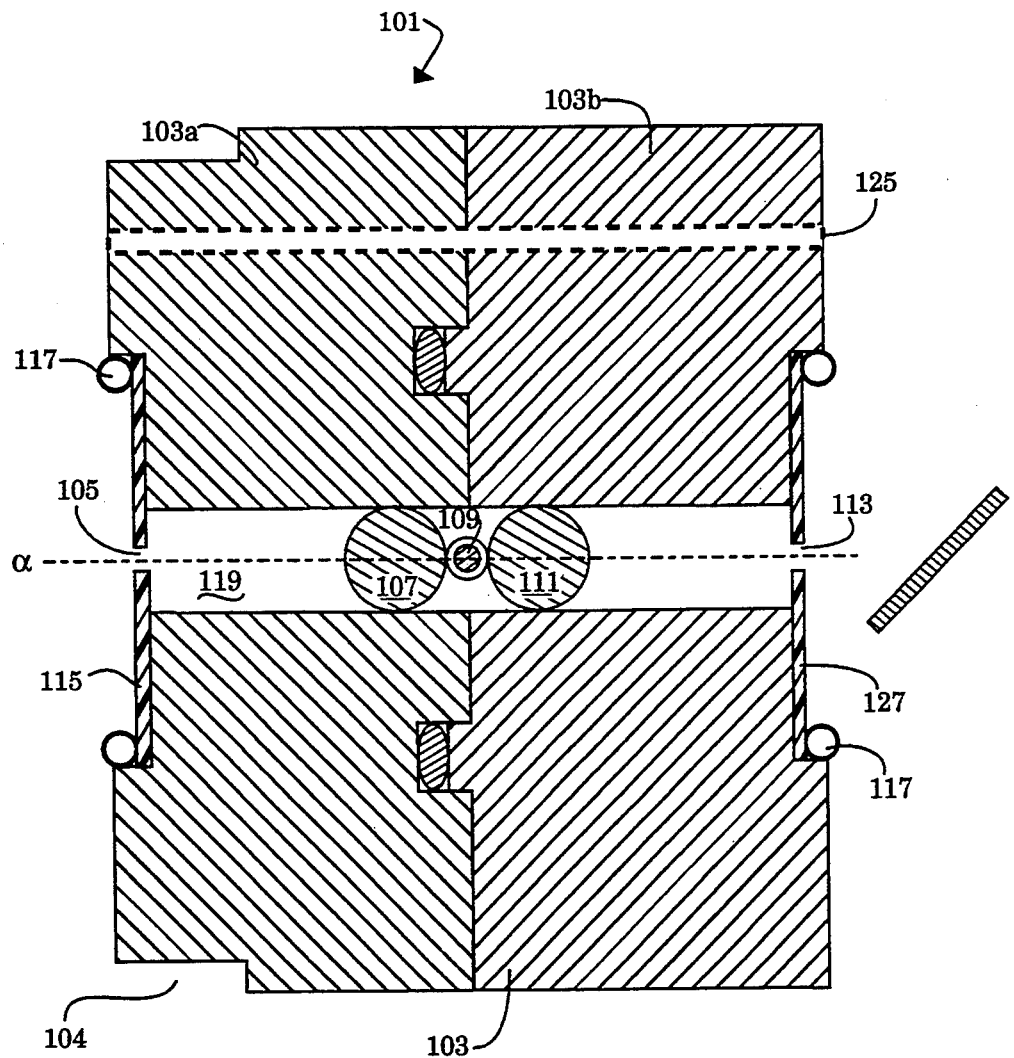
FIG. 5 shows a cross-sectional view of a capillary flowcell of this invention.

As shown in FIG. 5, the capillary flowcell 101 includes a holding means 103 having a bore 119 therethrough. A beam of electromagnetic radiation is focused and refocused by optical elements within the bore 119. A narrow beam of multiple wavelength electromagnetic radiation is preferentially transmitted along the optical axis $\alpha$ by the selection, focusing and reimaging of the optical elements.

A source of incident multiple wavelength electromagnetic radiation (not shown), typically a deuterium lamp or other source, is focused into a beam which includes multiple wavelengths of electromagnetic radiation. Preferably the beam is a convergent beam which is focused to pass through the entrance aperture, and which thereafter impinges completely upon the first lens.

The optical axis $\alpha$ is a line which is generally defined as the center of the path of multiple wavelength electromagnetic radiation as it is shaped by, in sequential order: (a) an entrance aperture 1015; (b) a first lens 107; (c) a capillary tube 109 having its long axis centered across the optical axis $\alpha$; and (d) a second lens 111. The first lens 107 focuses electromagnetic radiation incident from the aperture 105 to pass substantially through the inner diameter of the capillary tube 109. The second lens 111 focuses electromagnetic radiation which has passed through the capillary tube along the optical axis $\alpha$. The second lens 111 focuses electromagnetic radiation to pass through the exit aperture 113, if such an aperture is present, and/or focuses the radiation onto the entrance aperture of a polychromator. It is preferable that the convergent angle of the beam as it exits the flowcell matches the acceptance angle of the polychromator. The exit aperture 113 of the flowcell and the entrance aperture of the polychromator (not shown) can be the same port.

The diameter of the incident beam is first limited and shaped by the entrance aperture 105. As shown, each of the entrance aperture 105 and the exit aperture 113 is an opening within an aperture plate 115 and 127, respectively. In a preferred embodiment, the aperture plates 115 and 127 are held in place at a recessed surface of the holding means 103 by a retaining ring 117. This recessed aperture configuration acts to protect the aperture plate 115 and 127 while permitting the easy replacement of the aperture plate 115 and 127 if an aperture of different size is desired.

For ease of construction the aperture plate 115 and 127 can be made of plastic. Preferably, the diameter of the entrance aperture 105 is chosen to correspond to the maximum diameter of the image of the aperture 105 that will fit onto the inner diameter of the capillary 109. Preferably, the diameter of the exit aperture 113 is chosen to correspond to the maximum diameter of the image of the inner diameter of the capillary tube which will fit onto the entrance aperture of the polychromator.

As it passes through the entrance aperture 105, the beam enters a bore 119 within the holding means 103. Situated within this bore 119 are, in sequential order, a first lens 107, a capillary tube 109 having its long axis centered across the optical axis, and a second lens 111.

The first lens 107 and the second lens 111 are preferably spherical sapphire lenses. Sapphire lenses are preferred due to their ability to efficiently transmit electromagnetic radiation over the wavelength range of interest, their high index of refraction and ability to focus electromagnetic radiation over short focal lengths, and their reasonable cost.

The lenses are generally positioned by manufacturing the bore 119 somewhat smaller than the diameter of the lens. For example, a bore having a diameter of 1.95 mm would be formed to house a lens having a diameter of 2.0 mm. The spherical ball lens is then pressed into position within the bore 119. For this reason, a relatively soft material is preferably used for the holding means 103. Plastic such as Acetal is appropriate for use.

The first lens 107 is placed at an appropriate distance from each of the entrance aperture 105 and the capillary tube 109 so that light which enters the flowcell through the entrance aperture 105 is focused by the first lens to pass through the inner diameter of the capillary tube 109.

The capillary tube 109 is preferably a standard capillary tube. Such capillary tubes have an outside diameter (O.D.) of approximately 375 $\mu$m, and an inner diameter (I.D.) of approximately 50 $\mu$m. In one preferred embodiment, when a standard capillary tube is used, and the first lens 107 and second lens 111 are each a sapphire spherical ball lens having a diameter of 2.0 mm. The entrance aperture 105 is typically 0.5 to 0.6 mm in diameter, and is placed approximately 7 mm from the first lens. The capillary tube 109 is preferably placed so that it touches each of the first lens 107 and the second lens 111. The exit aperture 113 is preferably located approximately 7 mm from the second lens 111.

The second lens 111 is placed at an appropriate distance from each of the capillary tube 109 and the exit aperture 113 so that light which is incident upon the second lens 111 is focused to pass through the exit aperture 113.

In a preferred embodiment, as shown, the holding means includes two mating parts, 103a and 103b. A portion of the outer diameter of the first part 103a is preferably recessed so that the improved flowcell can be retained by a circular clamping hole in a standard multiple wavelength absorbance detector. The first part 103a includes the entrance aperture 105. Preferably, the entrance aperture 105 is located at the focal point of a convergent beam produced by the multiple wavelength electromagnetic radiation source. The first part 103a is configured to hold the first lens 107, preferably using a friction or pressure fit. The second part 103b is configured for holding the second lens 111 by a similar means. The second part 103b preferably includes an exit aperture 113. Light which passes through the exit aperture 113 enters a polychromator where the beam is split by wavelength, and the presence or absence of signal at the various wavelengths is determined. In a preferred embodiment, the diameter of the holding means is approximately 2 cm, and the length of the holding means is approximately 1.3 cm.

The first part 103a of the holding means 103 includes a recessed area which mates with a boss of the second part 103b. The two parts are positioned so that a hole 125 in each part aligns for entry of a screw (not shown). The screw maintains the holding means 103 as an integral unit.

Figure 6:
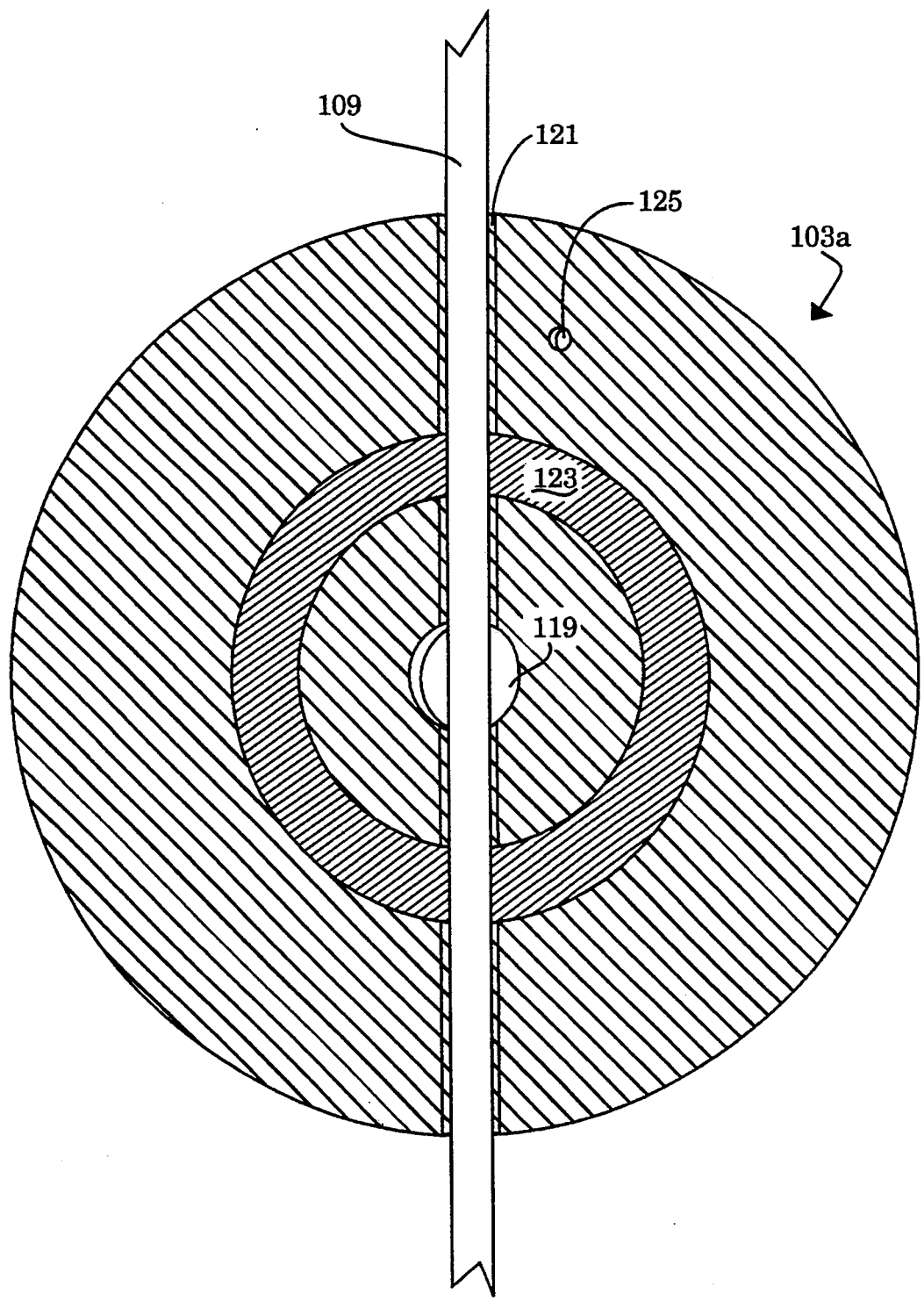
FIG. 6 shows the mating surface of one subunit of the flowcell of FIG. 5.

The capillary tube 109 is positioned so that the long axis of the tube is centered on the optic axis of the system. FIG. 6 shows the mating (inner) face of the first part 103a of the holding means 103. As shown in FIG. 5, the capillary tube 109 is held in position by a groove 121 in the first part 103a of the holding means 103. The groove 121 can have any desired cross-section, and is conveniently trapezoidal. The groove 121 substantially encloses the capillary tube 109. An O-ring 123 is held within a circular recessed trough on the mating face of one subunit. This O-ring 123 acts to help mate the two subunits, and to hold the capillary tube securely in place with a gentle pressure. The second subunit (not shown) mates with the first subunit to complete the holder apparatus, and the two subunits are conveniently held together using a pressure fit secured with a screw or the like. A threaded bore 125 for a screw is shown.

While the invention has been described in connection with specific embodiments thereof, those skilled in the art will recognize that various modifications are possible within the principles described herein. Such modifications, variations, uses, or adaptations of the invention, including such departures from the present disclosure as come within known or customary practice in the art, fall within the scope of the invention and of the appended claims.

I claim:

1. A capillary flowcell for determination of an analyte using converging multiple wavelength electromagnetic radiation, said flowcell comprising a holding means including an optical axis, the optical axis being defined by, in sequential order:
    (a) a first aperture located at the focal point of the converging multiple wavelength electromagnetic radiation;
    (b) a first spherical lens;
    (c) a capillary tube having its long axis centered across the optical axis; and
    (d) a second spherical lens;
wherein the first spherical lens focuses multiple wavelength electromagnetic radiation incident from the first aperture to pass through an inner diameter of the capillary tube; and
wherein the second spherical lens focuses electromagnetic radiation which has passed through the capillary tube.

2. A flowcell of claim 1, said flowcell comprising a holding means including an optical axis, the optical axis being defined by, in sequential order:
    (a) said first aperture;
    (b) said first spherical lens;
    (c) said capillary tube having its long axis centered across the optical axis;
    (d) said second spherical lens; and
    (e) a second aperture;
wherein the first spherical lens focuses multiple wavelength electromagnetic radiation incident from the first aperture to pass through an inner diameter of the capillary tube; and wherein the second spherical lens focuses multiple wavelength electromagnetic radiation to pass through the second aperture.

3. A flowcell of claim 2 wherein said second aperture is an entrance aperture of a polychromator.

4. A flowcell of claim 1 wherein at least one of the first spherical lens and the second spherical lens is sapphire.

5. A flowcell of claim 1 wherein the capillary tube is replaceable.

* * * * *